US011058562B2

(12) United States Patent
Pawlik et al.

(10) Patent No.: US 11,058,562 B2
(45) Date of Patent: Jul. 13, 2021

(54) PROSTHETIC SOCKET

(71) Applicant: OTTO BOCK HEALTHCARE PRODUCTS GMBH, Vienna (AT)

(72) Inventors: Roland Pawlik, Vienna (AT); Johan Nieuwendijk, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 115 days.

(21) Appl. No.: 16/097,188

(22) PCT Filed: Apr. 28, 2017

(86) PCT No.: PCT/EP2017/060169
§ 371 (c)(1),
(2) Date: Oct. 26, 2018

(87) PCT Pub. No.: WO2017/186901
PCT Pub. Date: Nov. 2, 2017

(65) Prior Publication Data
US 2019/0133793 A1    May 9, 2019

(30) Foreign Application Priority Data

Apr. 29, 2016  (DE) ..................... 10 2016 108 043.8

(51) Int. Cl.
*A61F 2/78*    (2006.01)
*A61F 2/80*    (2006.01)
(52) U.S. Cl.
CPC .............. *A61F 2/80* (2013.01); *A61F 2/7812* (2013.01); *A61F 2002/7818* (2013.01); *A61F 2002/7881* (2013.01)

(58) Field of Classification Search
CPC .. A61F 2/7812; A61F 2/80; A61F 2002/5026; A61F 2002/7875; A61F 2002/7881
USPC .......................................................... 623/36
See application file for complete search history.

(56) References Cited

U.S. PATENT DOCUMENTS

| 1,272,179 A | 7/1918 | Anderson et al. |
| 2,669,728 A | 2/1954 | Ritchie |
| 5,800,565 A | 9/1998 | Biedermann |
| 8,999,004 B2 | 4/2015 | Abu Osman et al. |
| 2010/0191348 A1 | 7/2010 | Kettwig et al. |
| 2013/0123940 A1 | 5/2013 | Hurley et al. |

(Continued)

FOREIGN PATENT DOCUMENTS

| DE | 9408556 U1 | 7/1994 |
| DE | 102007035410 A1 | 2/2009 |

(Continued)

OTHER PUBLICATIONS

PCT International Search Report for PCT International Patent Application No. PCT/EP2017/060169, dated Aug. 1, 2017.

*Primary Examiner* — Suba Ganesan
*Assistant Examiner* — Aren Patel
(74) *Attorney, Agent, or Firm* — Holland & Hart LLP

(57) ABSTRACT

A prosthetic socket, comprising a base for distal connection means for attaching a prosthesis component to the prosthetic socket and comprising at least one side wall, which extends from the base in the proximal direction and at least partially extends around a stump to be held in the prosthetic socket, and at least one support for fastening the side wall to the base being arranged on the base.

22 Claims, 3 Drawing Sheets

(56) References Cited

U.S. PATENT DOCUMENTS

| | | | |
|---|---|---|---|
| 2013/0289743 A1 | 10/2013 | Abu Osman et al. | |
| 2014/0121783 A1* | 5/2014 | Alley | A61F 5/0102 623/33 |
| 2014/0277584 A1 | 9/2014 | Hurley et al. | |
| 2015/0265434 A1 | 9/2015 | Hurley et al. | |
| 2016/0184112 A1* | 6/2016 | Radspieler | A61F 2/7843 623/36 |
| 2017/0056250 A1* | 3/2017 | Donovan | A61F 2/7812 |

FOREIGN PATENT DOCUMENTS

| | | |
|---|---|---|
| EP | 2629705 B1 | 10/2018 |
| GB | 675811 | 7/1952 |

\* cited by examiner

PROSTHETIC SOCKET

TECHNICAL FIELD

The invention relates to a prosthetic socket, comprising a base for distal connection means for attaching a prosthesis component and comprising at least one side wall, which extends from the base in the proximal direction and at least partially extends around a stump to be held in the prosthetic socket. Such a prosthetic socket suitable in particular for the care of amputation stumps or dysmelia, in order to provide a connection possibility for prosthetic components such as prosthetic knee joints, prosthetic feet, or prosthetic hands.

BACKGROUND

In order to fasten prosthesis components to a stump as securely as possible, most prosthetic sockets are individually produced. Generally, an impression of the stump is taken and a plaster positive is created from the impression, the plaster positive being used to shape the prosthetic socket, which generally consists of a plastic, optionally a fiber-reinforced plastic. A placeholder is applied to the positive in order to represent an elastic liner, which generally should be arranged between the prosthetic socket and the stump, so that there is an intermediate space between the outer periphery of the stump and the inner periphery of the socket. The prosthetic socket peripherally extends around the stump and has a proximal entry opening and a distal termination. Connection means for further prosthetic devices are arranged on or incorporated into said distal termination. Said connection means are, for example, pyramid adapters or similar devices by means of which, for example, prosthetic knee joints, prosthetic feet, or prosthetic hands can be fastened to the prosthetic socket. By means of this manner of production, the prosthetic socket is given the individually suitable periphery and the individually suitable length. Adjustability of the periphery or the socket length is neither necessary nor possible.

For adaptation to fluctuations in the stump volume of the prosthesis wearer, inflatable air cushions, hook-and-loop strips or a cable lacing according to EP 2 629 705 A1 can be arranged on a prosthetic socket or a prosthetic liner. DE 10 2007 035 410 A1 relates to a prosthetic socket for holding an amputation stump of an extremity, comprising connection means for a distal prosthesis device and comprising at least one shell, which has a curved, open cross-section and the shell ends of which at least partially overlap with each other in the worn state. At least one tightening means is arranged on the shell, which tightening means is effective in the peripheral direction and loads the shell ends toward each other.

SUMMARY

The problem addressed by the present invention is that of providing a prosthetic socket that can be produced by means of industrially prefabricated parts.

According to the invention, this problem is solved by means of a prosthetic socket having the features disclosed herein. Advantageous embodiments and further developments of the invention are disclosed in the description and the figures.

The prosthetic socket according to the invention, comprising a base for distal connection means for connecting a prosthesis component to the prosthetic socket and comprising at least one side wall, which extends from the base in the proximal direction and at least partially extends around a stump to be held in the prosthetic socket, provides that at least one support for fastening the side wall to the base is arranged on the base. Because according to the invention the prosthetic socket is divided into a distal prosthetic socket portion in the form of a base and a proximal socket portion in the form of at least one side wall or one side wall component, it is possible to adapt the two socket portions to each other and in particular to adjust the socket length. This can be accomplished, for example, by shortening the at least one support and/or the at least one side wall and reconnecting the shortened combination of the socket portions adapted to the particular user to each other. This makes it possible to adapt a prefabricated socket to an individual stump length and to establish the desired load on the end of the stump, particularly in the case of a thigh socket, in the case of which support can occur both at the ischium and at the end of the stump. Because of the length adaptability, the compressive force applied to the end of the stump can be varied, optionally also increased during the wearing duration, or adapted to the conditions at the stump over the wearing duration. For this purpose, it is advantageous if the side wall or side wall components can be releasably and reversibly fastened to the base. Unlike in the case of custom products, adjustability with respect to the length is necessary when prefabricated socket parts are used, i.e. prefabricated side walls or side wall components and the base.

In a further development of the invention, the base and the side wall, the side walls, or side wall components are designed in such a way that they can be fastened or fixed to each other in different positions. This makes it possible, for example, for one side wall to be fastened to the support higher, proceeding from the distal end of the support, than the other side wall so that individual adaptation to the stump can be achieved by simply sliding and fixing the side wall, the side walls, or the side wall components on the support.

A further development of the invention provides that the base is designed as a dimensionally stable cap or dimensionally stable plate at the distal end thereof or has such a cap or plate so that supporting, distal socket portions are formed on the base or the base has such supporting socket portions. The stump can be supported on one side of said dimensionally stable cap or plate, and the connection means for the distal prosthesis component can be arranged, formed, or fastened on the other side of said dimensionally stable cap or plate.

The base can have retaining devices for a liner worn on the stump in order to form an interface between the stump and the generally dimensionally stable prosthetic socket. In principle, it is also possible that retaining devices for the stump are formed or arranged on the prosthetic socket. The retaining devices for the liner can be designed as receiving elements for a pin, i.e. a pin lock, as it is known. It is also possible to secure the liner to the base by means of other interlocking elements or frictional connection elements. For example, magnets can be arranged on the base in order to fix a correspondingly configured liner, which likewise has magnets or ferromagnetic elements, to the base. It is also possible that clamping elements or clamping devices, retaining elements, or fixing devices, by means of which the liner is fastened, clamped, fixed, or secured to the side wall along the longitudinal extent of the liner, are arranged or formed on the side wall or the side wall components. Said retaining elements on the inside of the side wall likewise can be designed as interlocking elements or frictional connection elements, more particularly as protrusions, hook-and-loop fasteners, a climbing skin, nap velour, or magnets. Combinations of interlocking elements and frictional connection elements can also be arranged or formed both on the base and on the side wall or the side wall components.

A further development of the invention provides that the side wall is interlockingly fastened to the base. The side wall or the side wall components can be screwed to the base or fixed by means of latching elements, a bayonet coupling, or interlocking elements in the form of clips or other latching devices. The side wall can also be riveted to the base. Alternatively or additionally, the side wall can be fastened to the base or the support in a clamping manner so that the position of the side wall relative to the base is continuously adjustable.

The side wall can be formed from a plurality of side wall components and can have a tightening device, by means of which the side wall components can be aligned with each other or loaded against each other. Alternatively or additionally, two or more side walls can be formed, which can be aligned with each other or loaded toward each other by means of at least one tightening device. The tightening device can be designed as a belt, which is fastened to both side wall components and, by means of a length change, enables width adjustability of the two or more side wall components relative to each other. In principle, it is also possible that the side wall components are mounted on the base in such a way that the side wall components can be slid relative to each other, in order to enable adaptation to different stump sizes. The supports can be arranged opposite each other, for example on the medial side and the lateral side; in principle, it is possible and provided that the supports are arranged in different positions, for example anterior and posterior. In one embodiment of the invention, it is provided that at least one support is arranged on the medial side.

A further development of the invention provides that at least one support is foldably arranged on the base. If a plurality of supports is arranged or formed on the base, it can be provided either that all supports are foldably arranged on the base or that at least one support is rigidly connected to the base so that said support serves as a reference element. In order to adjust the prosthetic socket width and more easily put the prosthetic socket on, a support can be folded down together with a side wall component and thereby a peripheral expansion can be effected. The stump together with the liner is then inserted into the prosthetic socket and, for example, the distal end of the stump is set onto the inside of the distal base. The side wall component fixedly coupled to the base is laid against the liner and the side wall component foldably mounted on the base is folded toward the liner in order to thus enable the fixing of the stump together with the liner in the prosthetic socket. The two side wall components can overlap with each other in the edge regions so that the prosthetic socket completely extends around the stump to be held. In principle, it is also possible that there is a distance between the side edges of the side wall components, provided that the shape and the dimensional stability of the side wall components are sufficient to ensure secure holding of the stump in the prosthetic socket.

The support or the supports can be designed as a rail that extends away from the base in the proximal direction. The rails are preferably shorter than the side wall or the side wall components and can be shortened so that a smaller total socket length can be achieved.

Devices for interlockingly fixing the side wall can be arranged or formed in the support, more particularly in the rail. In particular, said devices are formed at discrete intervals in order to facilitate an association at discrete intervals. Alternatively, it is possible to provide slidable mounting with clamping retention, by means of an elongation hole formation either on the support or on the side wall. Besides a relatively coarse pattern by means of bores that are aligned with each other and that enable length shortening in corresponding larger intervals, a fine pattern can be formed on the support, which fine pattern engages with corresponding protrusions on the side wall or the side wall components, so that the length can be finely adjusted.

The side wall or the side wall component can have guides or receptacles, into which the support can be inserted. If the support is designed as a rail, the guides are designed as rail receptacles, which enable longitudinal slidability and insertion from outside so that there are three longitudinal degrees of freedom in total. By means of a corresponding design of the rail receptacle or receptacle of the support, there can be slidability only in the longitudinal extent of the support or of the rail receptacle, for example by means of a trapezoidal design of the rail or by means of a closed guide in the form of a sleeve. The guides and the supports are preferably equally long so that the guide is completely filled when the support is completely inserted in the guide. In order to shorten the socket length, both components must then be equally shortened.

Markings or material weakening points can be arranged or formed on the side wall and/or the support, by means of which markings or material weakening points predetermined breaking lines, predetermined cutting lines, or separation line specifications can be formed on the support and/or the side wall or the side wall component. In the case of the supports such a marking or material weakening point is arranged in the proximal region in particular, and in the case of the side wall or the side wall components such markings or material weakening points are arranged in the distal region in particular, in order to facilitate shortening and length adjustment. The markings or material weakening points are preferably formed peripherally or at least transversely to the longitudinal extent of the component in question.

The side wall or the side walls can be designed with different material stiffness and/or different material thicknesses. Thus, the at least one side wall does not have to consist of a single, homogeneous material with a constant material thickness. Rather, in one variant of the invention, it is provided that different materials are combined, that there are different material thicknesses in a side wall or side wall component, and/or that materials are treated differently in different regions in order to achieve different properties, in particular stiffnesses. For example, the side walls can be rigid in the region of the support, while the remaining regions can be elastic or equipped with flexible points in some regions.

At least two supports are arranged and formed on the base, of which supports one is oriented medially and one is oriented laterally on the base so that there is good lateral guidance. The wearing comfort of the prosthetic socket is not impaired at all, or only negligibly, by the medial-lateral arrangement of the support, because the dimensionally stable supports, which, for example, can be made of a steel or aluminum, cannot become noticeable with loading of the proximal prosthetic socket edge at the ischium during sitting or standing.

The side wall can have an open cross-section so that a peripheral adjustment can be realized in a simple manner by means of an adjustment system effective in the peripheral direction. In addition to length adjustability, can be realized by means of a tightening system, by means of which several side wall components are loaded against each other or a side wall having an open cross section is adjusted against each other, so that a variable region of overlap of the edges that are oriented in the peripheral direction results.

BRIEF DESCRIPTION OF THE DRAWINGS

Below, embodiments of the invention are explained in more detail by means of the enclosed figures. The figures show.

DETAILED DESCRIPTION

Figure 1:
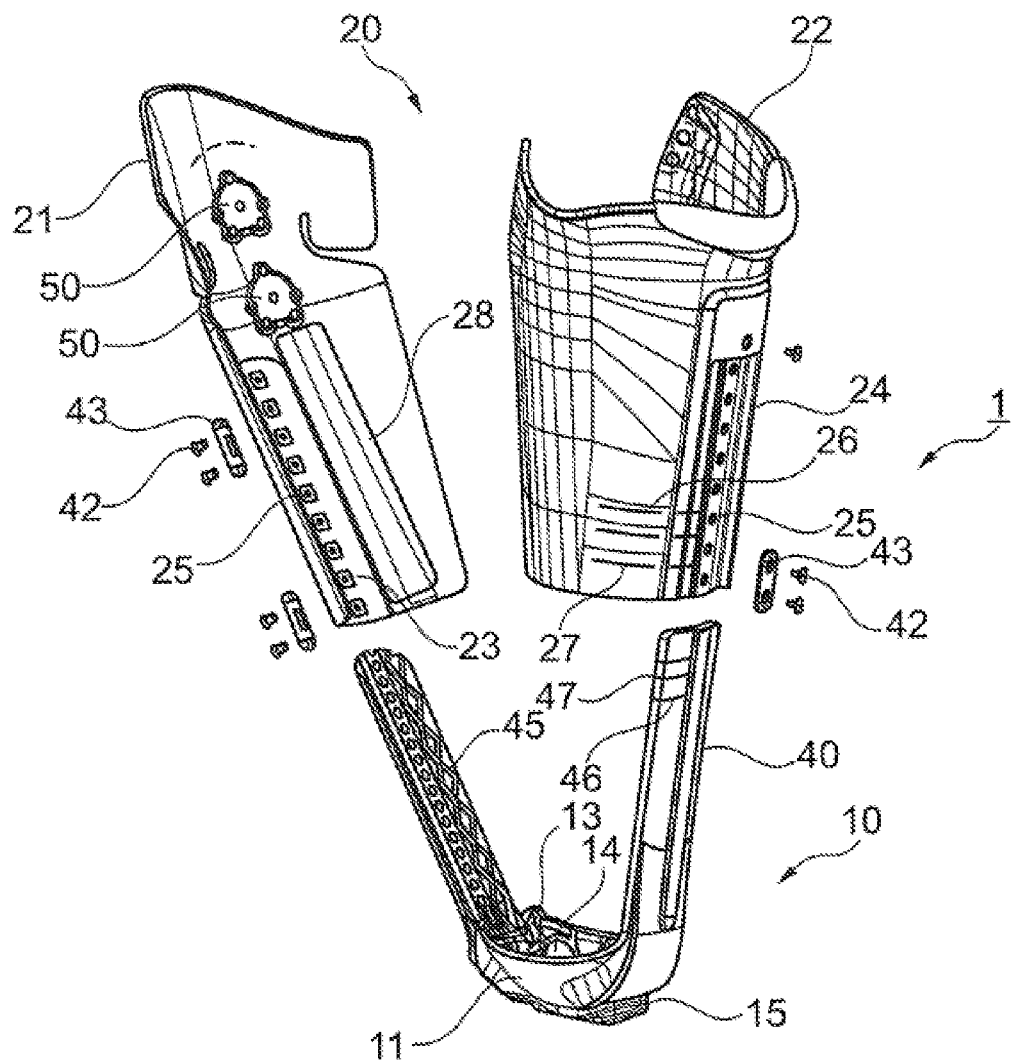
FIG. 1: the exploded view.

FIG. 1 shows an exploded view of a prosthetic socket 1, which has a base 10, to which two side wall components 21, 22 are releasably fastened. In the assembled and worn state, the two side wall components 21, 22 extend completely around the stump, which is not shown, and form a side wall 20 surrounding the stump. In an alternative embodiment, the side wall 20 can also be designed as a single part and can have either a closed cross-section or an open cross-section.

In the illustrated embodiment, the base 10 has, at the distal end thereof, a dimensionally stable cap 11, to the distal side of which connection means, which are not shown, for a further prosthesis component, such as a prosthetic knee joint, can be fastened. Said dimensionally stable cap 11 serves as a resting point for the end of the stump, which is not shown, and has at least one retaining device 14 for fastening or securing the stump or the liner worn on a stump to the prosthetic socket 1. In the illustrated embodiment, said retaining device 14 is designed as a hook-and-loop fastener component. In an alternative embodiment, other interlocking devices or a magnet securing means can be installed in order to secure the distal end of the liner to the base 10 and thus to the prosthetic socket by means of corresponding interlocking elements or ferromagnetic components.

Two supports 40, which are designed as rails, extend from the dimensionally stable cap 10 in the proximal direction. When the prosthetic socket 1 is worn, the supports 40 are positioned on the medial side and the lateral side of the stump and can have either the same length or different lengths, a greater length preferably being provided on the lateral side. Through-bores 45, as interlocking elements for fastening the side wall components 21, 22, are arranged within the supports 40 designed as rails. The through-bores 45 can be provided with a screw thread and are arranged one after the other at a defined spacing in the longitudinal extent of the supports 40. The laterally arranged support 40 is foldably arranged on the base 10 by means of a hinge 13, and the medial support 40 is formed integrally on the distal cap 41, so that an L-shaped, rigid main body is formed. Besides a pivotable mounting of the medial support 40, the medial support 40 can also be slidably arranged on the base 10 in order to enable adjustment of the stump width in the distal region. In principle, it is also possible to make both supports 40 foldable or also to rigidly arrange the medial support 40 on the dimensionally stable cap 11 or form the medial support 40 with the dimensionally stable cap 11. Also, more than two supports 40 can be formed or arranged on the base.

The side wall components 21, 22 and thus the entire side wall 20 are releasably fastened to the base 10. For this purpose, guides 23, 24 for the supports 40 are fastened to the outsides of the side wall components 21, 22. The guides 23, 24 are designed as rail receptacles, which are designed in correspondence with the rail-type designs of the supports 40 and can receive the same in said rail receptacles. The guides 23, 24 can be C-shaped, in which case the cross-section of the guides 23, 24 either permits lateral insertion of the supports 40 or has roof legs directed toward each other so that the supports 40 can be inserted into the corresponding guides 23, 24 only in the longitudinal extent. The side walls of the guide 23, 24 can also be inclined toward each other so that the supports 40 are fixed both in the medial direction and in the lateral direction but are still guided in the guides 23, 24 in such a way that the supports 40 can be slid in the longitudinal extent of the supports 40.

Bores having internal screw threads 25 are arranged in the guides 23, 24 in correspondence with the through-bores 45 in the supports 40, which internal screw threads 25 are arranged one after the other at intervals in the longitudinal extent, at which intervals said internal screw threads 25 are aligned with the through-bores 45. The side wall components 21, 22 are each connected to the associated support 40 by means of interlocking elements 42 in the form of screws. For this purpose, the supports 40 are inserted into the guides 23, 24 until the desired length is reached. The through-bores 45 and the internal screw threads 25 within the guides 23, 24 are aligned with each other and the screws 42 are pushed through and fixed. An interlocking, releasable fastening of the side wall 20 to the base 10 is thereby achieved. The through-bores 45 can also be designed as elongate holes in order to enable quasi-continuous adjustment of the position of the side wall components 21, 22 relative to the base 10. An elongate hole extending over the entire length can also be formed so that, besides an interlocking fixing of the side wall 20 on the supports 40, the longitudinal slidability along the guides 23, 24 is blocked in a clamping manner by means of the screws 42 and a washer 43.

In the distal region of the side wall components 21, 22, markings 26 and material weakening points 27 are applied oriented transversely to the longitudinal extent so that the total length can be shortened if necessary. The material weakening points 27 can extend over the entire periphery of the side wall component 21, 22; in the case of a single-piece design of the side wall 20, completely. The markings 26 are preferably aligned with each other at uniform intervals and can also be provided with a scale in order to facilitate length adaptation. Corresponding markings 46 and material weakening points 47 are arranged on the supports 40, preferably at the proximal ends thereof, and enable individual adaptability of the length of the whole prosthetic socket 1.

The side wall components 20, 21 form, as the side wall 20, a proximal socket portion, and the base 10 together with the supports 40 forms a distal socket portion, which socket portions are designed and arranged for longitudinal sliding relative to each other and fastening to each other, in such a way that said socket portions can be adjusted and fixed relative to each other continuously or discretely. By shortening the distal socket portion in the form of the base 10 and/or the proximal socket portion in the form of the side wall 20, a reduction of the socket length can be achieved, whereby it is possible to use industrially prefabricated socket parts in such a way that a prefabricated socket can be adapted to individual stump lengths. The desired load on the stump end can also be adapted and adjusted.

A tightening device 50, by means of which the socket width can be varied, for example by means of a lace-cable-belt system, is arranged on the lateral side wall component 21. Because of the two-part design of the side wall 20 in the illustrated embodiment and the foldable mounting of the lateral side wall component 21 on the base 10, it is possible and necessary to fix the position of the side wall components 21, 22 relative to each other in the peripheral direction. Because the base 10 can be folded and thus the prosthetic socket 1 can be widened, it is possible to facilitate the entry into the prosthetic socket. It is also thereby possible to arrange or form interlocking elements 28 on the inside of the side wall, which interlocking elements impede or prevent movement in the proximal direction. For example, a hook-and-loop fastener, a climbing skin, or a surface structuring, which interlockingly engages in a corresponding structure on the liner, can be arranged or formed on the inside of the side wall 20. By means of the folding-open motion, a peeling operation or disengagement can occur so that a corresponding separation of the prosthetic socket 1 and the liner can be easily accomplished.

In the embodiment shown in FIG. 1, the side wall components 21, 22 are designed differently. The medial side wall component 22 extends over more than half of the total periphery, here ¾ of the total periphery, while the lateral side wall component 21 is dimensioned in such a way that there is a periphery supplementation, so that the prosthesis stump can be completely surrounded. The side edges of the side wall components 21, 22 can overlap with each other in the worn and mutually fastened state and thereby allow width adjustment even during wearing, in the case of fluctuations in the stump volume.

Figure 2:
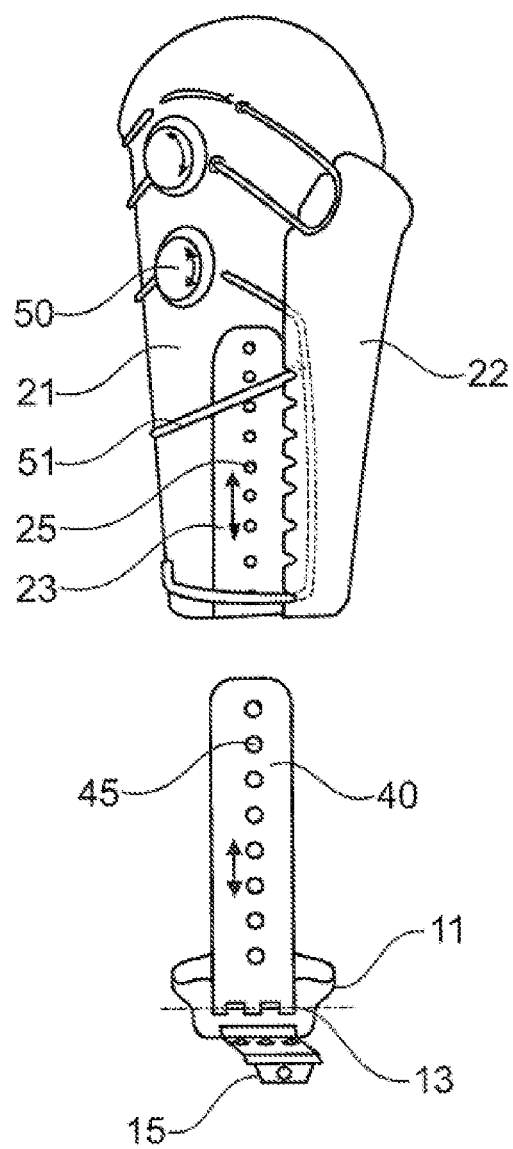
FIG. 2: a schematic side view in the unassembled state.

A prosthetic socket 1 before assembly, comprising a base 10 and a side wall 20, is shown in FIG. 2, in which the distal connection means 15 for a prosthesis component, for example in the form of a prosthetic knee joint, are arranged on the distal end of the base 10. The distal connection means 15 is designed as a receptacle of a pyramid adapter.

The side wall 20 is peripherally closed by means of the tightening device 50. The tightening device 50 is designed as a disk system, as it is known, in the case of which a belt system or cable system 51 can be tightened and relaxed by the rotation of a wheel. Width control can be accomplished by tightening the belt system or cable system 51.

In order to mount the side wall 20 on the base, the supports 40 are inserted into the guides. In the embodiment shown, only one guide 24 and one support 40 designed as a rail are visible because of the side view from the lateral direction. After the desired position has been reached, the screws 42 are screwed through the through-bores 45 and into the screw threads 25 in the guides 23, 24.

Figure 3:
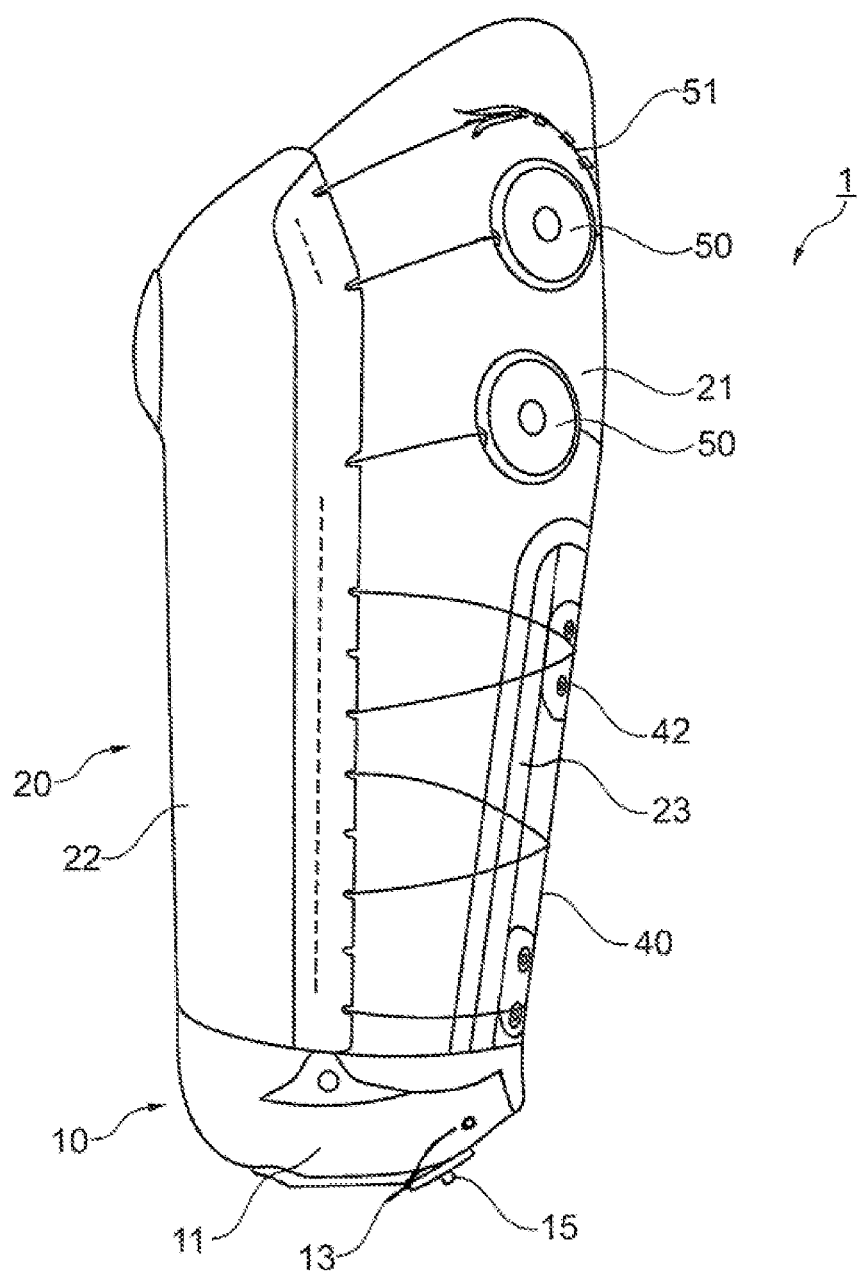

A finally assembled prosthetic socket 1 is shown in FIG. 3. The distal, dimensionally stable cap 11, the hinge device 13 for the lateral support 40, and the side wall 20, composed of a lateral side wall component 21 and a medial side wall component 22, are clear. In the embodiment shown, the tightening device 50 has two rotational mechanisms, by means of which the effective length of two cables 51 can be changed. The cables or bands 51 are arranged on the opposite side edges of the medial side wall component 22 and, by means of a shortening, cause a periphery reduction. By opposite rotation of the tightening devices 50, the periphery of the prosthetic socket can be enlarged. The lateral side wall component 21 is releasably fixed to the base 10 by means of four screws 42 in total.

The screws 42 are fed through the through-bores 45 in the support 40 and screwed into the internal screw threads 25 within the guide 23. An additional clamping effect results from the washer 43.

The invention claimed is:

1. A prosthetic socket, comprising:
    a base having distal connection members for attaching a prosthesis component to the prosthetic socket;
    a first side wall member, which extends from the base in a proximal direction and is configured to at least partially extend around a stump to be held in the prosthetic socket;
    a first support to fasten the first side wall member to the base;
    a second side wall member, which extends from the base in the proximal direction and is configured to at least partially extend around the stump, the second side wall member configured to at least partially overlap the first side wall member in a circumferential direction around the stump along a length of the first and second side members when the prosthetic socket is mounted to the stump;
    a second support to fasten the second side wall member to the base.

2. The prosthetic socket according to claim 1, wherein at least one of the first and second side wall members can be fastened to the base in different positions.

3. The prosthetic socket according to claim 1, wherein the base has a dimensionally stable cap or plate at a distal end thereof.

4. The prosthetic socket according to claim 1, further comprising at least one retaining device to retain a liner or the stump, the at least one retaining device being arranged on the base.

5. The prosthetic socket according to claim 4, wherein the at least one retaining device is designed as a magnet.

6. The prosthetic socket according to claim 1, wherein the first side wall member is interlockingly fastened to the base.

7. The prosthetic socket according to claim 1, wherein the first and second side wall members can be aligned with each other or loaded toward each other with at least one tightening device.

8. The prosthetic socket according to claim 1, wherein at least one of the first and second supports is foldably arranged on the base.

9. The prosthetic socket according to claim 1, wherein at least one of the first and second supports is designed as a rail extending in the proximal direction.

10. The prosthetic socket according to claim 1, further comprising interlocking elements to fasten the first and second side wall members to the first and second supports, respectively.

11. The prosthetic socket according to claim 1, further comprising at least one guide to receive at least one of the first and second supports is arranged on at least one of the first and second side wall members.

12. The prosthetic socket according to claim 1, wherein the first side wall member is fastened to the first support with interlocking elements.

13. The prosthetic socket according to claim 1, further comprising at least one of markings and material weakening points arranged or formed on at least one of the first and second side wall members and the first and second supports as predetermined breaking lines or predetermined cutting lines.

14. The prosthetic socket according to claim 1, wherein at least one of the first and second supports is arranged medially on the base and at least one of the first and second supports is arranged laterally on the base.

15. The prosthetic socket according to claim 1, wherein the first and second side wall members define a socket side wall having a cross-section that is discontinuous in a peripheral direction.

16. The prosthetic socket according to claim 1, wherein the first and second side wall members have at least one of different material stiffnesses and different material thicknesses.

17. The prosthetic socket according to claim 1, wherein at least one of the first and second supports pivotally fastens the respective first or second side wall member to the base.

18. A prosthetic socket, comprising:
- a base having at least one distal connection member configured to attach a prosthesis component to the prosthetic socket;
- a first side wall member extending from the base in a proximal direction and configured to at least partially extend around a stump that is positioned in the prosthetic socket;
- a first support to fasten the first side wall member to the base, the first support being arranged on the base;
- a second side wall member extending from the base in the proximal direction and configured to at least partially extend around the stump, the second side wall member configured to at least partially overlap the first side wall member in a circumferential direction around the stump along a length of the first and second side members when the prosthetic socket is mounted to the stump;
- a second support to fasten the second side wall member to the base, the second support being arranged on the base.

19. The prosthetic socket according to claim 18, wherein at least one of the first and second side wall members is configured to be fastened to the base in different positions.

20. The prosthetic socket according to claim 18, wherein the base has a dimensionally stable cap or plate at a distal end thereof.

21. The prosthetic socket according to claim 18, further comprising at least one retaining device configured to receive a liner or the stump, the at least one retaining device being arranged on the base.

22. The prosthetic socket according to claim 18, wherein at least one of the first and second support pivotally fastens the respective first or second side wall member to the base.

* * * * *